(12) United States Patent
Deckman et al.

(10) Patent No.: US 7,874,986 B2
(45) Date of Patent: *Jan. 25, 2011

(54) METHODS AND DEVICES FOR VISUALIZATION AND ABLATION OF TISSUE

(75) Inventors: Robert K. Deckman, San Bruno, CA (US); Craig Gerbi, Mountain View, CA (US); Michael Munrow, Belmont, CA (US); Jessica Grossman, San Francisco, CA (US)

(73) Assignee: Gynesonics, Inc., Redwood City, CA (US)

( * ) Notice: Subject to any disclaimer, the term of this patent is extended or adjusted under 35 U.S.C. 154(b) by 274 days.

This patent is subject to a terminal disclaimer.

(21) Appl. No.: 11/564,164

(22) Filed: Nov. 28, 2006

(65) Prior Publication Data

US 2007/0249936 A1 Oct. 25, 2007

Related U.S. Application Data

(63) Continuation-in-part of application No. 11/409,496, filed on Apr. 20, 2006, now Pat. No. 7,815,571.

(51) Int. Cl.
*A61B 8/00* (2006.01)
*A61H 1/00* (2006.01)
*A61B 18/18* (2006.01)

(52) U.S. Cl. ............... 600/439; 600/437; 601/2; 606/41; 606/46

(58) Field of Classification Search .............. None
See application file for complete search history.

(56) References Cited

U.S. PATENT DOCUMENTS

| 4,289,132 A | 9/1981 | Rieman |
| 4,802,487 A | 2/1989 | Martin et al. |
| 4,936,281 A | 6/1990 | Stasz |
| 5,372,587 A | 12/1994 | Hammerslag et al. |

(Continued)

FOREIGN PATENT DOCUMENTS

WO   WO 97/17105   5/1997

(Continued)

OTHER PUBLICATIONS

Alterovitz et al., "Simulating Needle Insertion and Radioactive Seed Implantation for Prostate Brachytherapy," *Medicine Meets Virtual Reality* 11, Westwood et al. (Eds.), IOS Press, Jan. 2003, pp. 19-25.

(Continued)

*Primary Examiner*—Long V Le
*Assistant Examiner*—Angela M Hoffa
(74) *Attorney, Agent, or Firm*—Townsend and Townsend and Crew LLP

(57) ABSTRACT

Delivery systems, and methods using the same, having an ultrasound viewing window for improved imaging and a needle for ablation treatment of target tissues. In an embodiment, the target tissue is a fibroid within a female's uterus. In an embodiment the delivery system includes a rigid shaft having a proximal end, and a distal end, and an axial passage extending through the rigid shaft. In an embodiment, the axial passage is configured for removably receiving the ultrasound imaging insert having an ultrasound array disposed on a distal portion.

26 Claims, 14 Drawing Sheets

U.S. PATENT DOCUMENTS

| | | |
|---|---|---|
| 5,456,689 A | 10/1995 | Kresch et al. |
| 5,471,988 A | 12/1995 | Fujio et al. |
| 5,492,126 A | 2/1996 | Hennige et al. |
| 5,527,331 A | 6/1996 | Kresch et al. |
| 5,531,676 A | 7/1996 | Edwards et al. |
| 5,649,911 A | 7/1997 | Trerotola |
| 5,666,954 A | 9/1997 | Chapelon et al. |
| 5,697,897 A | 12/1997 | Buchholtz et al. |
| 5,730,752 A | 3/1998 | Alden et al. |
| 5,741,287 A | 4/1998 | Alden et al. |
| 5,769,880 A | 6/1998 | Trukai et al. |
| 5,860,974 A | 1/1999 | Abele |
| 5,863,294 A | 1/1999 | Alden |
| 5,873,828 A | 2/1999 | Fujio et al. |
| 5,876,340 A | 3/1999 | Tu et al. |
| 5,876,399 A | 3/1999 | Chia et al. |
| 5,891,137 A | 4/1999 | Chia et al. |
| 5,906,615 A | 5/1999 | Thompson |
| 5,916,198 A | 6/1999 | Dillow |
| 5,957,941 A | 9/1999 | Ream |
| 5,964,740 A * | 10/1999 | Ouchi ............... 604/264 |
| 5,979,452 A | 11/1999 | Fogarty et al. |
| 5,979,453 A | 11/1999 | Savage et al. |
| 5,984,942 A | 11/1999 | Alden et al. |
| 6,002,968 A | 12/1999 | Edwards |
| 6,007,499 A | 12/1999 | Martin et al. |
| 6,032,673 A | 3/2000 | Savage et al. |
| 6,039,748 A | 3/2000 | Savage et al. |
| 6,059,766 A | 5/2000 | Greff |
| 6,077,257 A | 6/2000 | Edwards et al. |
| 6,141,577 A | 10/2000 | Rolland et al. |
| 6,146,378 A | 11/2000 | Mikus et al. |
| 6,146,380 A | 11/2000 | Racz et al. |
| 6,158,250 A | 12/2000 | Tibbals, Jr. et al. |
| 6,171,249 B1 * | 1/2001 | Chin et al. ............... 600/461 |
| 6,190,383 B1 | 2/2001 | Schmaltz et al. |
| 6,193,714 B1 | 2/2001 | McGaffigan et al. |
| 6,211,153 B1 | 4/2001 | Garnick et al. |
| 6,238,336 B1 * | 5/2001 | Ouchi ............... 600/160 |
| 6,254,601 B1 | 7/2001 | Burbank et al. |
| 6,280,441 B1 | 8/2001 | Ryan |
| 6,296,639 B1 | 10/2001 | Truckai et al. |
| 6,306,129 B1 | 10/2001 | Little et al. |
| 6,315,741 B1 | 11/2001 | Martin et al. |
| 6,379,348 B1 | 4/2002 | Onik |
| 6,405,732 B1 | 6/2002 | Edwards et al. |
| 6,419,648 B1 | 7/2002 | Vitek et al. |
| 6,419,653 B2 | 7/2002 | Edwards et al. |
| 6,419,673 B1 | 7/2002 | Edwards et al. |
| 6,425,867 B1 | 7/2002 | Vaezy et al. |
| 6,432,067 B1 | 8/2002 | Martin et al. |
| 6,447,477 B2 | 9/2002 | Burney et al. |
| 6,463,331 B1 | 10/2002 | Edwards |
| 6,482,203 B2 | 11/2002 | Paddock et al. |
| 6,485,413 B1 | 11/2002 | Boppart et al. |
| 6,506,154 B1 | 1/2003 | Ezion et al. |
| 6,506,156 B1 | 1/2003 | Jones et al. |
| 6,506,171 B1 | 1/2003 | Vitek et al. |
| 6,507,747 B1 | 1/2003 | Gowda et al. |
| 6,508,815 B1 | 1/2003 | Strul et al. |
| 6,522,142 B1 | 2/2003 | Freundlich |
| 6,540,677 B1 | 4/2003 | Angelsen et al. |
| 6,543,272 B1 | 4/2003 | Vitek |
| 6,550,482 B1 | 4/2003 | Burbank et al. |
| 6,554,780 B1 | 4/2003 | Sampson et al. |
| 6,559,644 B2 | 5/2003 | Froundlich et al. |
| 6,569,159 B1 | 5/2003 | Edwards et al. |
| 6,572,613 B1 | 6/2003 | Ellman et al. |
| 6,589,237 B2 | 7/2003 | Woloszko et al. |
| 6,592,559 B1 | 7/2003 | Pakter et al. |
| 6,602,251 B2 | 8/2003 | Burbank et al. |
| 6,610,054 B1 | 8/2003 | Edwards et al. |
| 6,612,988 B2 | 9/2003 | Maor et al. |
| 6,613,004 B1 | 9/2003 | Vitek et al. |
| 6,613,005 B1 | 9/2003 | Friedman et al. |
| 6,623,481 B1 | 9/2003 | Garbagnati et al. |
| 6,626,854 B2 | 9/2003 | Friedman et al. |
| 6,626,855 B1 | 9/2003 | Weng et al. |
| 6,632,193 B1 | 10/2003 | Davison et al. |
| 6,635,055 B1 | 10/2003 | Cronin |
| 6,635,065 B2 | 10/2003 | Burbank et al. |
| 6,638,275 B1 | 10/2003 | McGaffigan |
| 6,638,286 B1 | 10/2003 | Burbank et al. |
| 6,645,162 B2 | 11/2003 | Friedman et al. |
| 6,645,202 B1 | 11/2003 | Pless et al. |
| 6,652,516 B1 | 11/2003 | Gough |
| 6,660,002 B1 | 12/2003 | Edwards et al. |
| 6,660,024 B1 | 12/2003 | Flaherty et al. |
| 6,663,624 B2 | 12/2003 | Edwards et al. |
| 6,663,626 B2 | 12/2003 | Truckai et al. |
| 6,666,833 B1 | 12/2003 | Friedman et al. |
| 6,679,855 B2 | 1/2004 | Horn et al. |
| 6,685,639 B1 | 2/2004 | Wang et al. |
| 6,689,128 B2 | 2/2004 | Sliwa, Jr. et al. |
| 6,692,490 B1 | 2/2004 | Edwards |
| 6,701,931 B2 | 3/2004 | Sliwa, Jr. et al. |
| 6,705,994 B2 | 3/2004 | Vortman et al. |
| 6,712,815 B2 | 3/2004 | Sampson et al. |
| 6,716,184 B2 | 4/2004 | Vaezy et al. |
| 6,719,755 B2 | 4/2004 | Sliwa, Jr. et al. |
| 6,728,571 B1 | 4/2004 | Barbato |
| 6,730,081 B1 | 5/2004 | Desai |
| 6,735,461 B2 | 5/2004 | Vitek et al. |
| 6,743,184 B2 | 6/2004 | Sampson et al. |
| 6,746,447 B2 | 6/2004 | Davison et al. |
| 6,764,488 B1 | 7/2004 | Burbank et al. |
| 6,773,431 B2 | 8/2004 | Eggers et al. |
| 6,790,180 B2 | 9/2004 | Vitek |
| 6,805,128 B1 | 10/2004 | Pless et al. |
| 6,805,129 B1 | 10/2004 | Pless et al. |
| 6,813,520 B2 | 11/2004 | Truckai et al. |
| 6,832,996 B2 | 12/2004 | Woloszko et al. |
| 6,837,887 B2 | 1/2005 | Woloszko et al. |
| 6,837,888 B2 | 1/2005 | Ciarrocca et al. |
| 6,840,935 B2 | 1/2005 | Lee |
| 6,936,048 B2 | 8/2005 | Hurst |
| 6,994,706 B2 | 2/2006 | Chornenky et al. |
| 7,517,346 B2 | 4/2009 | Sloan et al. |
| 2001/0014805 A1 | 8/2001 | Burbank et al. |
| 2001/0051802 A1 | 12/2001 | Woloszko et al. |
| 2002/0002393 A1 | 1/2002 | Mitchell |
| 2002/0022835 A1 | 2/2002 | Lee |
| 2002/0052600 A1 | 5/2002 | Davison et al. |
| 2002/0068871 A1 | 6/2002 | Mendlein et al. |
| 2002/0077550 A1 | 6/2002 | Rabiner et al. |
| 2002/0183735 A1 | 12/2002 | Edwards et al. |
| 2003/0009164 A1 | 1/2003 | Woloszko et al. |
| 2003/0014046 A1 | 1/2003 | Edwards |
| 2003/0028111 A1 | 2/2003 | Vaezy et al. |
| 2003/0032896 A1 | 2/2003 | Bosley et al. |
| 2003/0130575 A1 | 7/2003 | Desai |
| 2003/0130655 A1 | 7/2003 | Woloszko et al. |
| 2003/0195420 A1 | 10/2003 | Mendlein et al. |
| 2003/0195496 A1 | 10/2003 | Maguire et al. |
| 2003/0199472 A1 | 10/2003 | Al-Hendy et al. |
| 2003/0216725 A1 | 11/2003 | Woloszko et al. |
| 2003/0216759 A1 | 11/2003 | Burbank et al. |
| 2004/0002699 A1 | 1/2004 | Ryan et al. |
| 2004/0006336 A1 | 1/2004 | Swanson |
| 2004/0030268 A1 | 2/2004 | Weng et al. |
| 2004/0054366 A1 | 3/2004 | Davison et al. |
| 2004/0120668 A1 | 6/2004 | Loeb |
| 2004/0143252 A1 | 7/2004 | Hurst |
| 2004/0153057 A1 | 8/2004 | Davison |

| | | | |
|---|---|---|---|
| 2004/0175399 A1 | 9/2004 | Schiffman | |
| 2004/0176760 A1 | 9/2004 | Qiu | |
| 2004/0193028 A1 | 9/2004 | Jones et al. | |
| 2004/0215182 A1 | 10/2004 | Lee | |
| 2004/0230190 A1 | 11/2004 | Dahla et al. | |
| 2004/0254572 A1 | 12/2004 | McIntyre et al. | |
| 2005/0038340 A1 | 2/2005 | Vaezy et al. | |
| 2005/0107781 A1 | 5/2005 | Ostrovsky et al. | |
| 2005/0124882 A1 | 6/2005 | Ladabaum et al. | |
| 2005/0149013 A1 | 7/2005 | Lee | |
| 2005/0177209 A1 | 8/2005 | Leung et al. | |
| 2005/0197577 A1 | 9/2005 | Makin et al. | |
| 2005/0215990 A1 | 9/2005 | Govari | |
| 2005/0216039 A1 | 9/2005 | Lederman | |
| 2005/0228288 A1 | 10/2005 | Hurst | |
| 2005/0255039 A1 | 11/2005 | Desai | |
| 2005/0256405 A1 | 11/2005 | Makin et al. | |
| 2006/0010207 A1 | 1/2006 | Akerman et al. | |
| 2006/0058680 A1* | 3/2006 | Solomon | 600/466 |
| 2006/0178665 A1 | 8/2006 | Sloan | |
| 2006/0189972 A1* | 8/2006 | Grossman | 606/32 |
| 2007/0006215 A1 | 1/2007 | Epstein et al. | |

FOREIGN PATENT DOCUMENTS

| | | |
|---|---|---|
| WO | WO 98/11834 | 3/1998 |
| WO | WO 98/14169 | 4/1998 |
| WO | WO 99/43366 | 9/1999 |
| WO | WO 00/00098 | 1/2000 |
| WO | WO 01/80723 A2 | 11/2001 |
| WO | WO 01/95819 A1 | 12/2001 |
| WO | WO 02/11639 A1 | 2/2002 |
| WO | WO 03/005882 A2 | 1/2003 |
| WO | WO 03/005882 A3 | 1/2003 |
| WO | WO 03/065908 A1 | 8/2003 |
| WO | WO 2004/002293 A2 | 1/2004 |
| WO | WO 2004/002550 A2 | 1/2004 |
| WO | WO 2004/020011 A1 | 3/2004 |
| WO | WO 2004/035110 A2 | 4/2004 |
| WO | WO 2004/058328 A2 | 7/2004 |
| WO | WO 2004/064658 | 8/2004 |

OTHER PUBLICATIONS

Bergamini et al., "Laparoscopic Radiofrequency Thermal Ablation: A New Approach to Symptomatic Uterine Myomas," *Am. J. Obstetrics and Gynecology* (2005) 192: 768-73.

CNN.com Health Women, "Experimental technique uses lasers to shrink uterine fibroids," Nov. 28, 2000.

Hindley et al.; "MRI guidance of focused ultrasound therapy of uterine fibroids: Early results," *American Journal of Roentgenology*, 2004, 183(6): 1173-1719.

Kanaoka et al., "Microwave endometrial ablation at a frequency of 2.45 Ghx. A pilot study," *J Reprod Med.* Jun. 2001; 46(60): 559-63.

Law et al., "Magnetic resonance-guided percutaneous laser ablation of uterine fibroids," *J Magn Reson Imaging*, Oct. 2000; 12(4):565-70.

Liu et al., "Catheter-Based Intraluminal Sonography," *J. Ultrasound Med.*, 2004, 23:145-160.

Mogami et al., "Usefulness of MR-guided percutaneous cryotherapy," *Med. Imaging Technol.* 2004, 22(3): 131-6. (English abstract).

MSNBC OnLine Articles, About Us: Articles; "Intrauterine Fibroids Can Now Be Treated Nonsurgically".

Okamura et al., "Force Modeling for Needle Insertion into Soft Tissue," *IEEE Transactions on Biomedical Engineering*, Oct. 2001, 10 (51): 1707-1716.

RSNA 2000 Explore News Release; "Lasers Liquefy Uterine Fibroid Tumors," 11:30 a.m. CST, Monday, Nov. 27, 2000.

Senoh et al., "Saline Infusion Contrast Intrauterine Sonographic Assessment of the Endometrium with High-Frequency, Real-Time Miniature Transducer Normal Menstrual Cycle: a Preliminary Report," *Human Reproduction*, 14 (10): 2600-2603, 1999.

Vascular and Interventional Radiology, SRSC; *Nonsurgical Treatment of Uterine Fibroids*.

Websand, Inc., *New treatment options for fibroid tumors*, Copyright 2002 by WebSand, Inc.

* cited by examiner

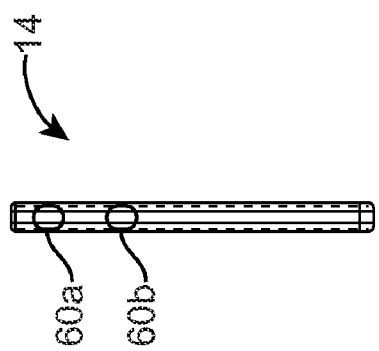
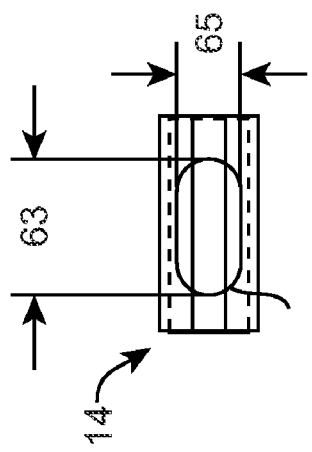
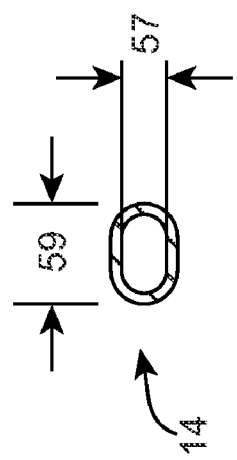
FIG. 5C
FIG. 5B
FIG. 5A

METHODS AND DEVICES FOR VISUALIZATION AND ABLATION OF TISSUE

CROSS REFERENCE TO RELATED APPLICATIONS

The present application is a continuation-in-part of U.S. patent application Ser. No. 11/409,496 filed Apr. 20, 2006, entitled "Rigid Delivery Systems Having Inclined Ultrasound and Curved Needle", the disclosure of which is incorporated herein by reference, in its entirety.

FIELD OF INVENTION

The present invention relates generally to medical systems and methods. More particularly, the invention relates to delivery systems having an ultrasound probe for improved imaging and curved needle for ablation treatment and methods for using the same.

BACKGROUND OF THE INVENTION

Treatment of the female reproductive tract and other conditions of dysfunctional uterine bleeding and fibroids remain with unmet clinical needs. Fibroids are benign tumors of the uterine myometria (muscle) and are the most common tumor of the female pelvis. Fibroid tumors affect up to 30% of women of childbearing age and can cause significant symptoms such as discomfort, pelvic pain, mennorhagia, pressure, anemia, compression, infertility, and miscarriage. Fibroids may be located in the myometrium (intramural), adjacent the endometrium (submucosal), or in the outer layer of the uterus (subserosal). Most common fibroids are a smooth muscle overgrowth that arise intramurally and can grow to be several centimeters in diameter.

Current treatments for fibroids include either or both pharmacological therapies and surgical interventions. Pharmacological treatments includes the administration of medications such as NSAIDS, estrogen-progesterone combinations, and GnRH analogues. All medications are relatively ineffective and are palliative rather than curative.

Surgical interventions include hysterectomy (surgical removal of the uterus) and myomectomy. Surgical myomectomy, in which fibroids are removed, is an open surgical procedure requiring laparotomy and general anesthesia. Often these surgical procedures are associated with the typical surgical risks and complications along with significant blood loss and can only remove a portion of the culprit tissue.

To overcome at least some of the problems associated with open surgical procedures, laparoscopic myomectomy was pioneered in the early 1990's. However, laparoscopic myomectomy remains technically challenging, requiring laparoscopic suturing, limiting its performance to only the most skilled of laparoscopic gynecologists. Other minimally invasive treatments for uterine fibroids include hysteroscopy, uterine artery ablation, endometrial ablation, and myolysis.

While effective, hysterectomy has many undesirable side effects such as loss of fertility, open surgery, sexual dysfunction, and long recovery time. There is also significant morbidity (sepsis, hemorrhage, peritonitis, bowel and bladder injury), mortality and cost associated with hysterectomy. Hysteroscopy is the process by which a thin fiber optic camera is used to image inside the uterus and an attachment may be used to destroy tissue. Hysteroscopic resection is a surgical technique that uses a variety of devices (loops, roller balls, bipolar electrodes) to ablate or resect uterine tissue. The procedure requires the filling of the uterus with fluid for better viewing and thus has potential side effects of fluid overload. Hysteroscopic ablation is limited by its visualization technique and thus, only appropriate for fibroids which are submucosal and/or protrude into the uterine cavity.

Uterine artery embolization was introduced in the early 1990's and is performed through a groin incision by injecting small particles into the uterine artery to selectively block the blood supply to fibroids and refract its tissue. Complications include pelvic infection, premature menopause and severe pelvic pain. In addition, long term MRI data suggest that incomplete fibroid infarction may result in regrowth of infarcted fibroid tissue and symptomatic recurrence.

Endometrial ablation is a procedure primarily used for dysfunctional (or abnormal) uterine bleeding and may be used, at times, for management of fibroids. Endometrial ablation relies on various energy sources such as cryo, microwave and radiofrequency energy. Endometrial ablation destroys the endometrial tissue lining the uterus, and although an excellent choice for treatment of dysfunctional uterine bleeding, it does not specifically treat fibroids. This technique is also not suitable treatment of women desiring future childbearing.

Myolysis was first performed in the 1980's using lasers or radio frequency (RF) energy to coagulate tissue, denature proteins, and necrose myometrium using laparoscopic visualization. Laparoscopic myolysis can be an alternative to myomectomy, as the fibroids are coagulated and then undergo coagulative necrosis resulting in a dramatic decrease in size. As with all laparoscopic techniques, myolysis treatment is limited by the fact that it can only allow for visualization of subserosal fibroids.

Needle myolysis uses a laparoscope, percutaneous, or open technique to introduce one or more needles into a fibroid tumor under direct visual control. Radio frequency current, cryo energy, or microwave energy is then delivered between two adjacent needles (bipolar), or between a single needle and a distant dispersive electrode affixed to the thigh or back of the patient (unipolar). The aim of needle myolysis is to coagulate a significant volume of the tumor, thereby cause substantial shrinkage. The traditional technique utilizes making multiple passes through different areas of the tumor using the coagulating needle to destroy many cylindrical cores of the abnormal tissue. However, the desirability of multiple passes is diminished by the risk of adhesion formation which is thought to escalate with increasing amounts of injured uterine serosa, and by the operative time and skill required. Myolysis can be an alternative to myomectomy, as the fibroids are coagulated and then undergo coagulative necrosis resulting in a dramatic decrease in size. Myolysis is generally limited by its usage with direct visualization techniques, thus being limited to the treatment of subserosal fibroids.b monologue To overcome the limitations of current techniques, it would be desirable to provide a minimally invasive approach to visualize and selectively eradicate fibroid tumors within the uterus. The present invention addresses these and other unmet needs.

BRIEF SUMMARY OF THE INVENTION

The present invention is directed to delivery systems, and methods using the same, having an ultrasound probe for improved imaging and a needle for ablation treatment of target tissues. In an embodiment, the needle is curved with the ultrasound probe having an ultrasound array at a distal portion. In an embodiment, the target tissue is a fibroid within a female's uterus. In an embodiment the delivery system includes a rigid shaft having a proximal end, a distal end, and an axial passage extending through the rigid shaft. In an embodiment, the axial passage is configured for removably receiving an ultrasound imaging insert having the ultrasound array disposed at a distal portion. As can be appreciated, the viewing mechanism may be of any other suitable type such as Optical Coherence Topography (OCT).

A needle extends adjacent an exterior surface of the rigid delivery shaft and is configured to deliver to the target site radio frequency energy (or other ablative energy such as, but not limited to, electromagnetic energy including microwave, resistive heating, cryogenic) generated at a relatively low power and for relatively a short duration of active treatment time. In an embodiment, the needle is disposed within a needle guide which extends along an exterior of the rigid shaft. In an embodiment, the needle has a hollow body and a solid distal tip formed from conductive material. The needle, optionally, may be covered, at least along a distal portion of the needle body, with a sheath. In an embodiment, the sheath is retractable such that the needle distal tip is extendable from a sheath's distal end thereby adjusting the length of the exposed conductive distal tip. In an embodiment, the sheath is formed from non-conductive material such as Parylene ®.

The target site undergoing treatment may be any target site which may benefit from the treatment devices and methods according to the present invention. Usually the target site is a uterus within a female's body. The target site in need of treatment generally has an initial (e.g. prior to treatment) approximate diameter which is greater than about two (2) centimeters ("cm"). Usually, the target site's initial diameter ranges from about 1 to about 6 cm. Normally the initial untreated diameter is about 2 cm.

In an embodiment of methods according to the present invention for visualization and ablation of fibroid tissues needing treatment within a patient's body include providing a visualization and ablation system according the device and system embodiments described herein. An ultrasound imaging, embodying features of the present invention is inserted within the axial passage of the rigid shaft with the distal portion of the imaging insert conforming to a shaft distal portion. Under the guidance of the imaging system, the needle is inserted into the tissue site. The RF generator is set to deliver and/or maintain a target temperature at the target site for a treatment period.

In an embodiment, the power and temperature are generated by a radio frequency energy generator. The radio frequency energy generator is generally configured to deliver energy at a power from about 1 to about 50 watts ("W"), generally from about 1 to about 40 W, usually from about 20 to about 40 W, and normally about 30 W. The radio frequency energy generator is further configured to provide a target temperature at the target site ranging from about 50 to about 110 degrees Celsius ("° C."), usually from about 60 to about 100° C., normally about 90° C. In an embodiment, the needle's conductive tip is at approximately body temperature as it is initially disposed within the patient's body.

In an embodiment, the target site is treated for a period of time ranging from about 1 to about 10 minutes, generally from about 1 to about 8 minutes, usually from about 3 to about 8 minutes, normally about 6 minutes.

In an embodiment, at least one fluid lumen extends along the rigid shaft for delivering fluids to a distal portion of the delivery system. The at least one fluid lumen may be configured for delivery of any one or more of fluids such as those for enhancing acoustic coupling between the ultrasound imaging insert and the target site, contrasting dyes, therapeutic agents, and the like. In an embodiment, the at least one fluid lumen includes acoustic coupling lumens including an internal lumen extending along the axial passage and terminating at an internal port within its distal end and an external lumen extending along the axial passage and terminating at an external port in fluid communication with the outside of the axial lumen. In an embodiment, the external lumen is formed by an external hollow tubular body extending along the needle guide, while the internal lumen is formed by an internal hollow tubular body extending along the underside of the axial hollow tubular body forming the axial passage. It should be appreciated, however, that the external and internal fluid lumens may be oriented in any other suitable location along the shaft. In the embodiment, as shown, the external lumen is located along the needle guide such that the fluid may exit near the ultrasound window, while the internal lumen extends along the underside of the axial hollow tubular body which forms the axial passage so as to allow the fluid to be delivered to the inner tip without trapping air inside the shaft.

In an embodiment, the present invention includes a visualization and ablation system generally having a delivery device, an ultrasound imaging probe detachable from the delivery system, a radio frequency energy generator, and an ultrasound system. An exemplary delivery system having inclined ultrasound and ablation needle is described in more detail in co-pending U.S. patent application Ser. No. 11/409, 496, filed Apr. 20, 2006, which is assigned to the assignee of the present application and incorporated herein by reference in its entirety.

BRIEF DESCRIPTION OF THE DRAWINGS

The following drawings should be read with reference to the detailed description. Like numbers in different drawings refer to like elements. The drawings illustratively depict embodiments including features of the present invention. The drawings are not necessarily drawing to scale and are not intended to limit the scope of the invention.

FIGS. 5A through 5C illustrate the exemplary features of an ablation needle for use with the visualization and ablation system of FIGS. 4A-4C.

DETAILED DESCRIPTION OF THE INVENTION

Figure 1A:
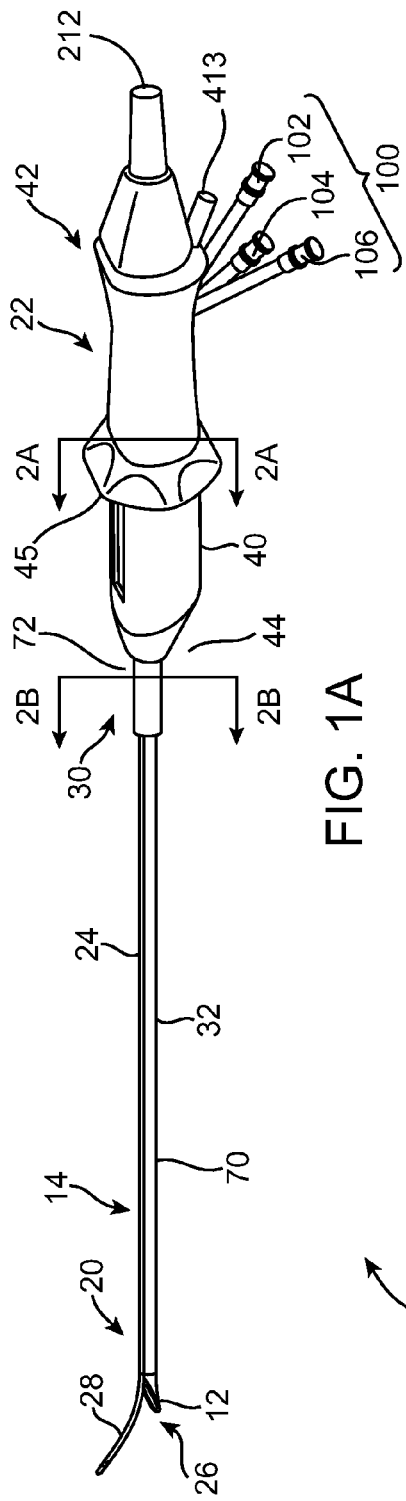
FIGS. 1A through 1C illustrate an exemplary delivery system embodying features of the present invention and having an inclined ultrasound array for improved imaging and a curved needle for ablation treatment.
Figure 1B:
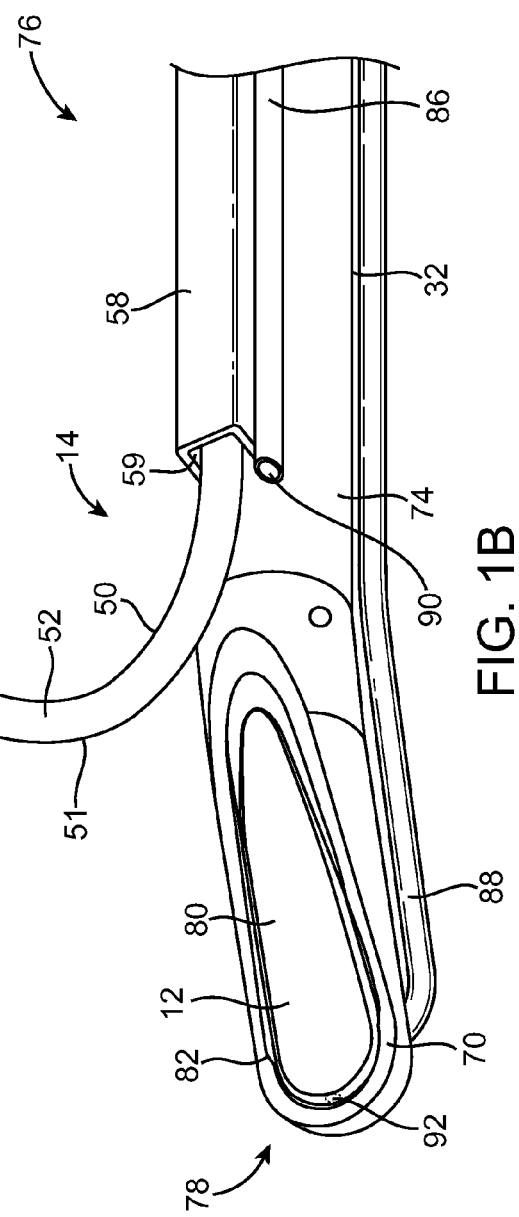
Figure 1C:
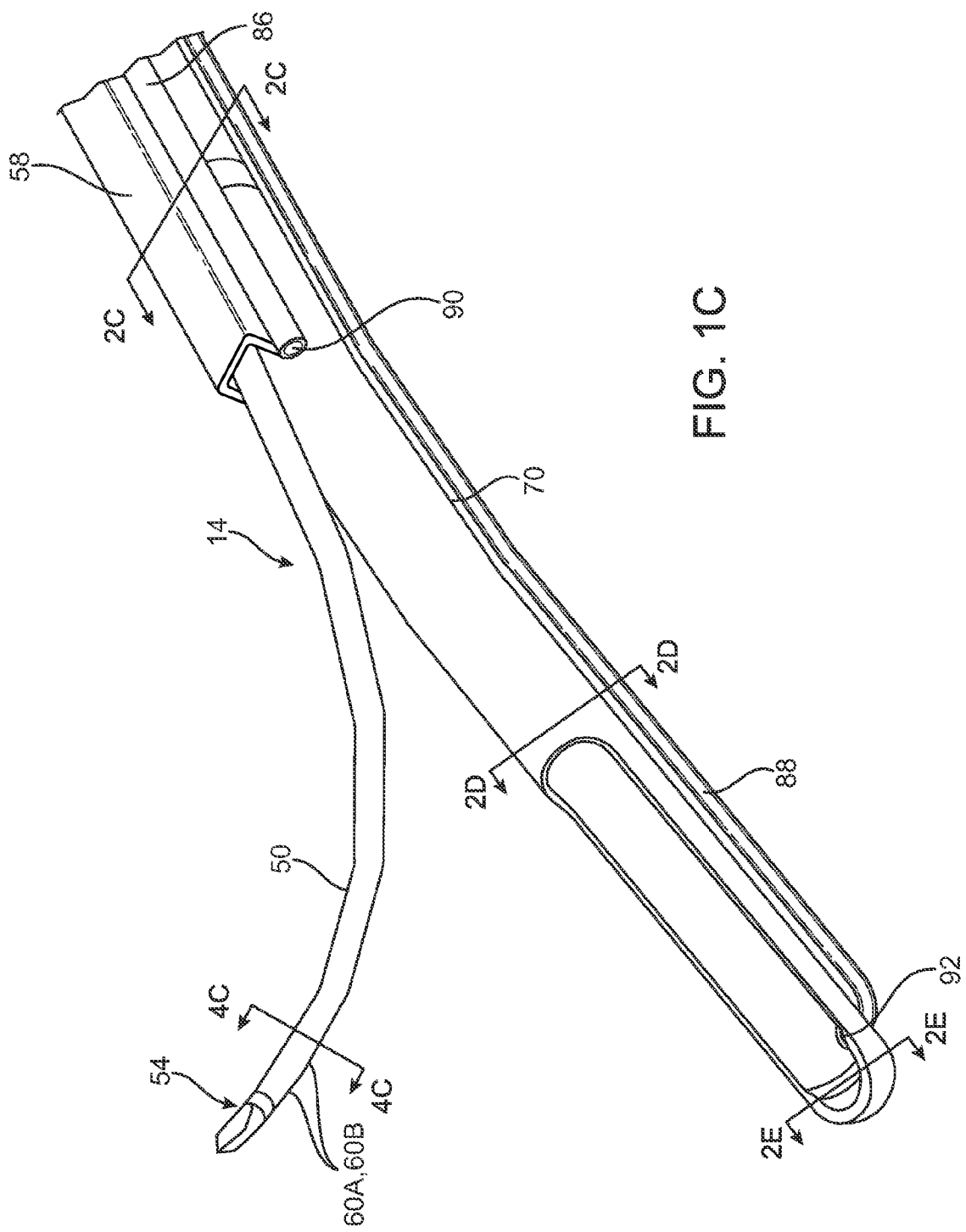

Referring to FIGS. 1A through 1C, an exemplary delivery system 10 embodying features of the present invention is shown having a shaft inclined viewing window 12 for improved imaging and a curved needle 14 for ablation treatment of a target site 16 such as fibroid tissues 18 (FIG. 3E) within a female's reproductive system. The delivery system 10 includes a system distal end 20, a system proximal end 22, and a rigid delivery shaft 24. Delivery shaft 24 includes a shaft distal end 26 with a bent or deflectable shaft distal tip 28, a shaft proximal end 30, and an axial passage 32 extending longitudinally through at least a portion of the delivery shaft 24. A handle 40 with handle proximal and distal ends, 42 and 44, is attachable to the shaft proximal end 30. The handle 40 further includes a longitudinally movable slider 45 for enabling the advancement and retraction of the needle 14 to and from within a needle guide 58.

The curved needle 14 has a needle body 50 with a shaped needle distal end 52 and a solid needle distal tip 54, as best seen in FIGS. 1B, 1C and 4A-C. Needle 14 is configured to deliver, to the target site 16 including fibroid 18 (as shown in FIG. 3E), radio frequency energy generated at a relatively low power and for relatively a short duration of time from an ablative energy generator 400 (such as, but not limited to, electromagnetic energy including microwave, resistive heating, cryogenic) including a radio frequency (RF) energy generator 410, as shown in and discussed in reference to FIGS. 3A and 3E. In an embodiment, as shown, needle body 50 is a hollow body forming a needle lumen 51.

Figure 2A:
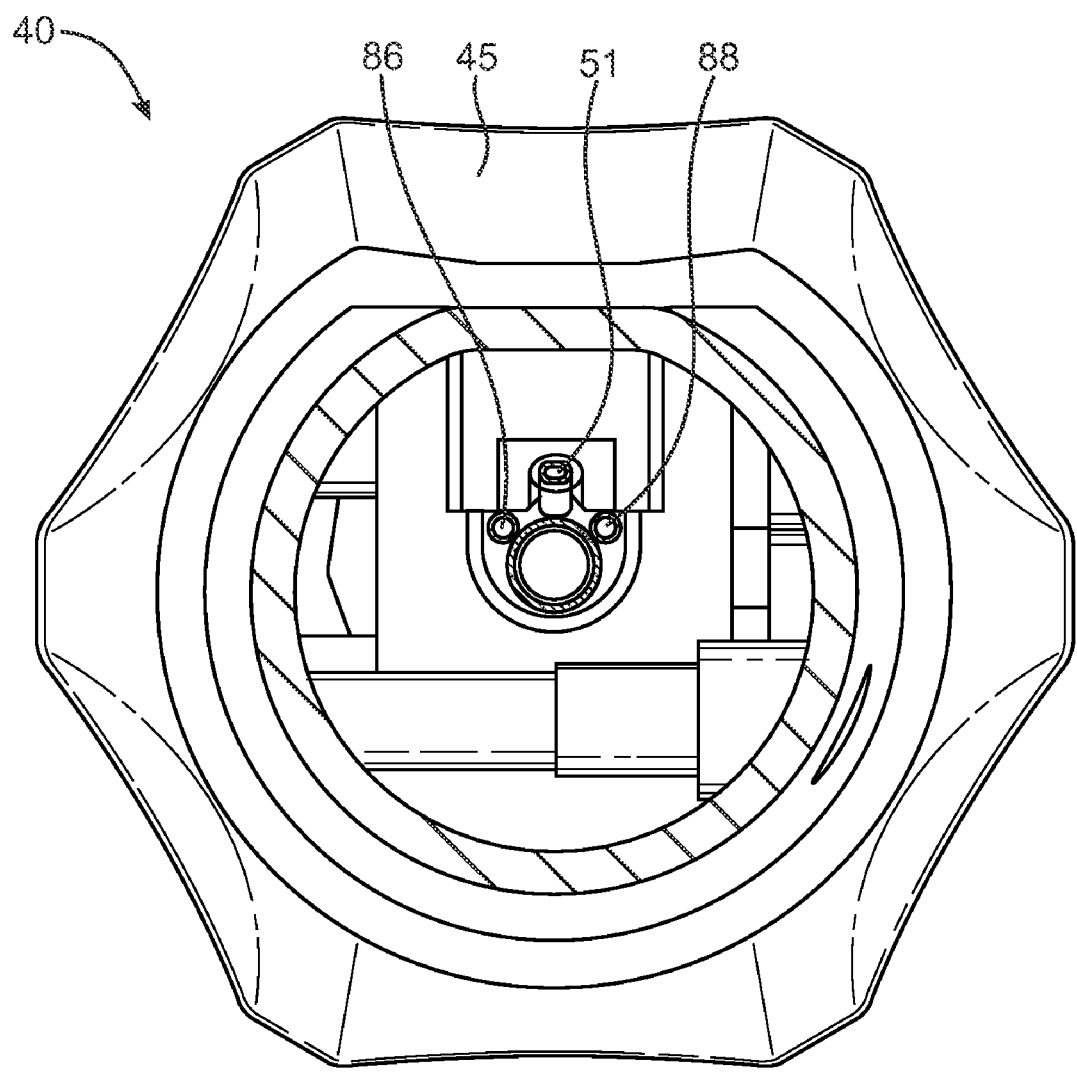
FIGS. 2A through 2E illustrate cross-sectional views of the embodiments of exemplary delivery system of FIGS. 1A through 1C taken along their respective lines.
Figure 2B:
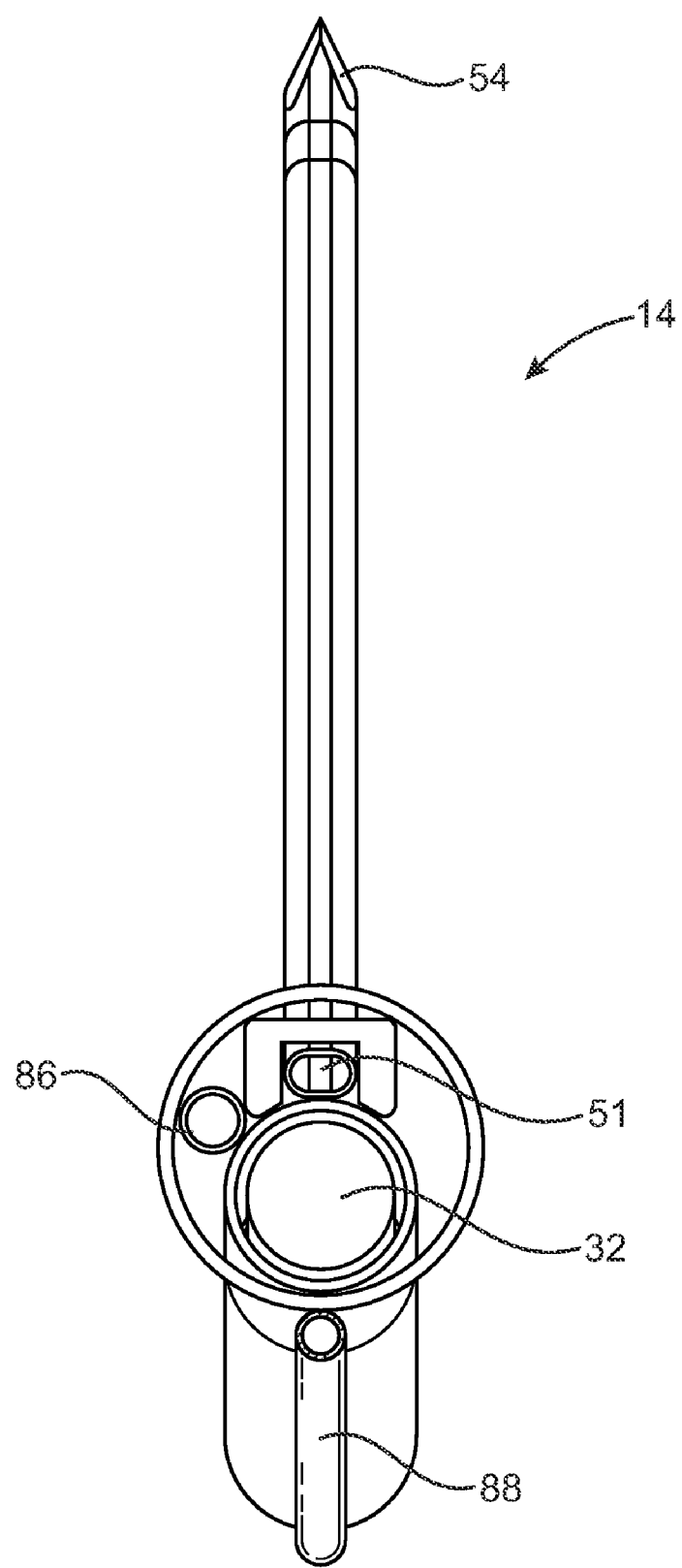
Figure 2C:
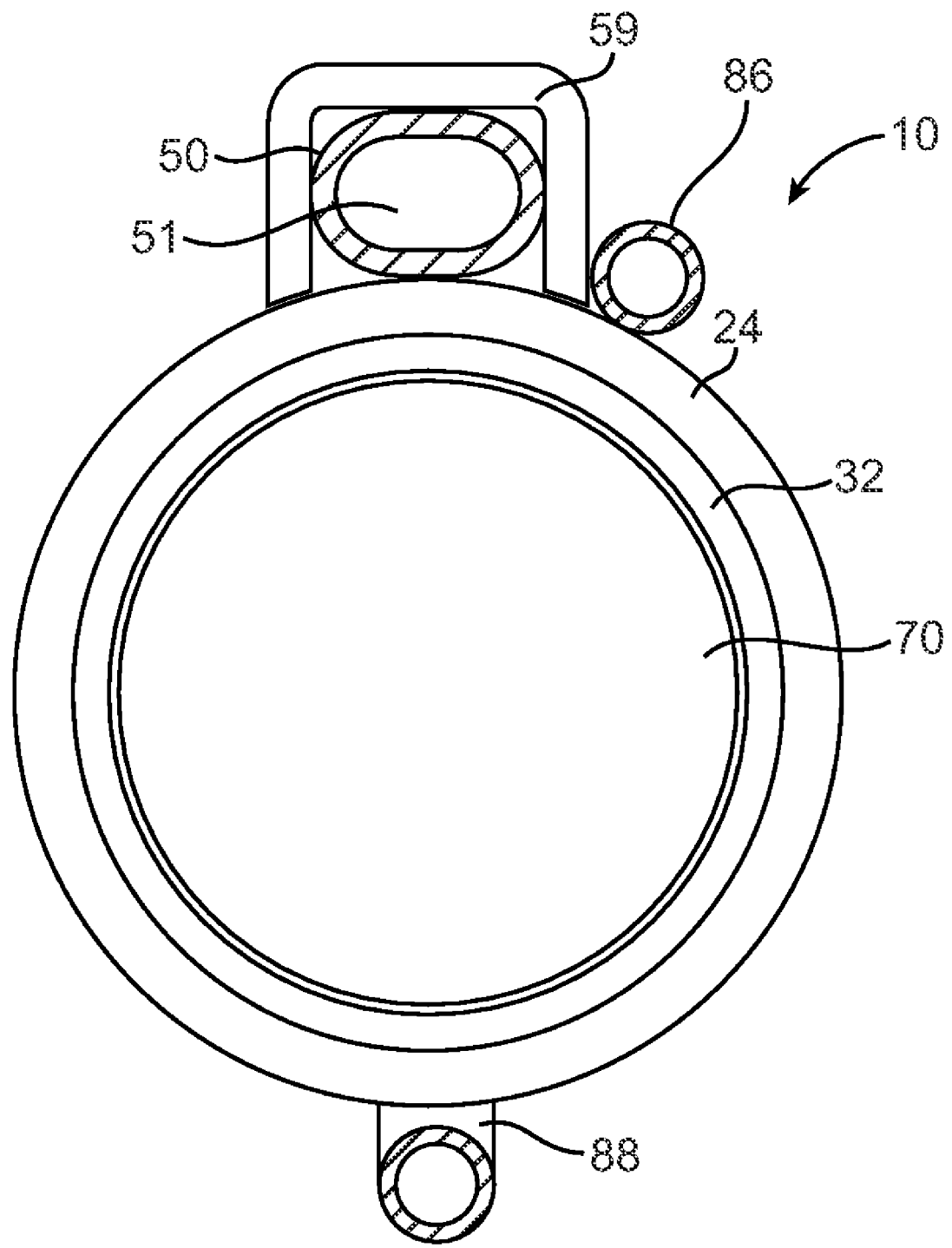
Figure 2D:
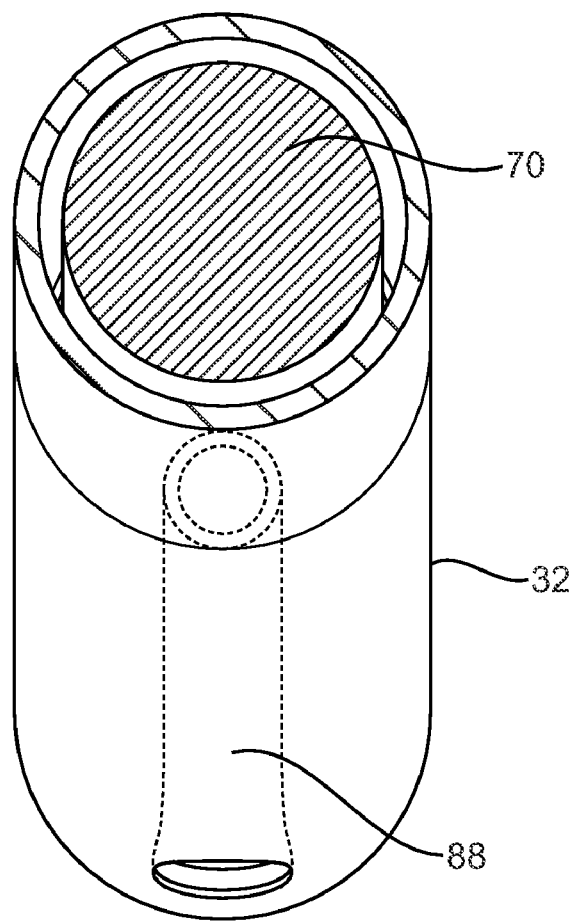
Figure 2E:
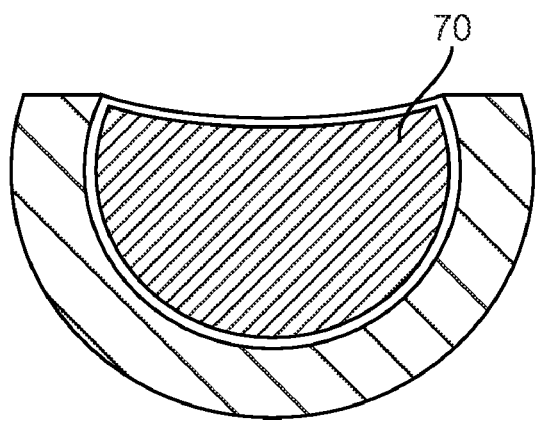

Now referring back to FIGS. 1A and 1B, needle 14 is disposed adjacent the exterior of the shaft 24 within the needle guide 58. Needle guide 58 includes a guide passage 59 and is attachable to the shaft by way of adhesive, or other means such as laser welding, shrink tubing, and the like. Needle 14, as best seen in FIGS. 1B, 1C, 4B, and 5C, may include one or more needle apertures 60. As shown, the needle 14 includes two needle apertures 60A and 60B. The most distal aperture 60A exposes the distal end of a thermocouple pair 59a and 59b as shown in FIG. 4C. The proximal aperture 60B may be used for delivery of various therapeutic and/or imaging enhancement fluids and contrasting agents/dyes to the target site 16 and fibroid 18. In the embodiment shown, contrasting dye runs within the lumen 51 of the hollow needle body. As can be seen from FIGS. 2A and 4C, the thermocouple pair 59a and 59b are disposed within the lumen 51 for monitoring the temperature at the target site 16, while the annular space around the thermocouples within lumen 51 is usable for delivery of dyes.

The shaft axial passage 32 is configured for removably and replaceably receiving and housing an ultrasound imaging insert 70. A sealing element 72 may be provided between the ultrasound imaging insert 70 and the shaft handle 40 to provide sufficient sealing around the imaging insert 70 at a proximal end.

The ultrasound imaging insert 70 as shown in FIG. 1B, and as further described below, comprises an insert flexible shaft 74, an insert proximal end 76, an insert distal end 78, an ultrasound array 80 having a flat surface, and an insert flat viewing window 82 disposed at the insert distal end 78. The ultrasound array 80 is viewable through the shaft viewing window 12 which has a flat inner surface inclined relative to a longitudinal axis of the shaft. The flat inner surface shaft viewing window may be used for axial and/or rotational orientation of the ultrasound imaging insert 70 within the delivery system shaft 24. The flat surface of the insert comes into full contact with the flat inner surface of the shaft after the insert is fully received in an axial passage of the shaft.

The delivery system 10, as shown in various FIGS. 1 and 2, at the device proximal end 22, includes a plurality of fluid inlet ports 100 in fluidic communication with various portions of the delivery system shaft 24, needle 14, and/or imaging insert 70. In an embodiment features of which are shown in FIG. 1A and 2A, system 10, includes fluid inlet ports 102, 104, and 106. Fluid inlet ports 100 (including 102, 104, and 106) are configured to direct various fluids to a distal portion 23 of the delivery system 10. By way of example, fluid inlet port 102 is configured to deliver dyes to at least one of the needle apertures 60, such as aperture 60B at the needle distal end 52; while fluid inlet ports 104 and 106 are configured, respectively, to deliver acoustic coupling fluids through external and internal axial lumens 86 and 88 disposed along axial passage 32 to a shaft external fluid outlet port 90 and a shaft internal fluid outlet port 92 at the shaft distal end 26. Same or different fluid ports, such as fluid port 102, may be further utilized to deliver other fluids such as therapeutic agents to any of the other outlet ports or apertures. Optionally, additional apertures may be provided at desired locations along lumen 51 of the hollow needle body 50.

The shaft 24 of the present invention as described herein may serve several functions including delivering ultrasound, diagnostic, and/or interventional treatments, bending of the ultrasound insert via the deflectable distal tip, and/or providing a sterile barrier between the ultrasound and/or interventional components. As shown in FIG. 1B, the delivery shaft 24 carries the ultrasound imaging insert 70 within its axial passage 32.

Generally, the delivery system shaft 24 will have a length in a range from about 20 cm to about 40 cm and an outer diameter in a range from about 3 mm to about 10 mm, while the ultrasound imaging insert 70 will have a length in a range from about 50 cm to about 90 cm and an outer diameter in a range from about 2 mm to about 4 mm. Delivery system Shaft 24 and the ultrasound imaging insert 70 may be acoustically coupled in one or more of several ways to enable the effective passage of ultrasound energy from one component to the other. For example, the ultrasound insert 70 may be placed in close mechanical contact with the shaft 24 so as to provide a dry coupling. In addition or alternatively, a thin compliant layer (e.g., pad or sheet) may be disposed between the viewing windows 82 and 12, of the ultrasound insert 70 and the shaft 24, respectively, so as to provide further interference between such components. It will be appreciated that a thinner layer may be preferred to minimize unwanted acoustic loss, index of refraction, impedance, and/or other material property effects. Alternatively, or in addition to, the shaft axial passage 32 in which the ultrasound imaging insert 70 is disposable, may be filled with a fluid (e.g., water or oil) or gel to further provide a wet coupling between the shaft and the imaging insert which may compensate for any mechanical tolerances.

Figure 3A:
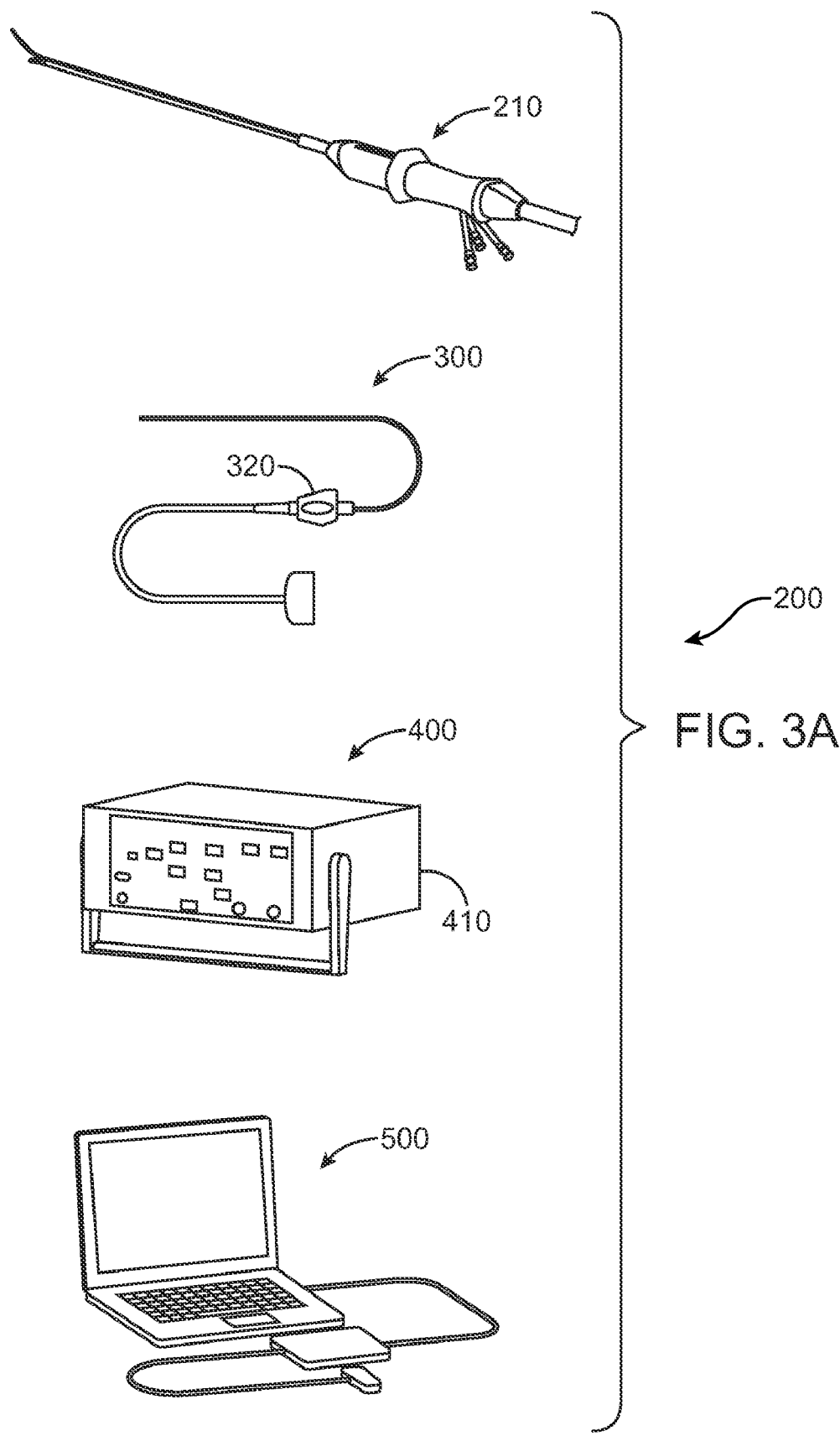
FIGS. 3A illustrates a visualization and ablation system embodying features of the present invention.

Now referring to FIG. 3A, a visualization and ablation system 200 embodying features of the present invention is shown, including a delivery device 210, an ultrasound imaging probe 300 being detached from the delivery system 210, the radio frequency energy generator 410, and an ultrasound system 500. The various components of the exemplary visualization and ablation system 200 will be further described in individual detail.

Figure 3B:
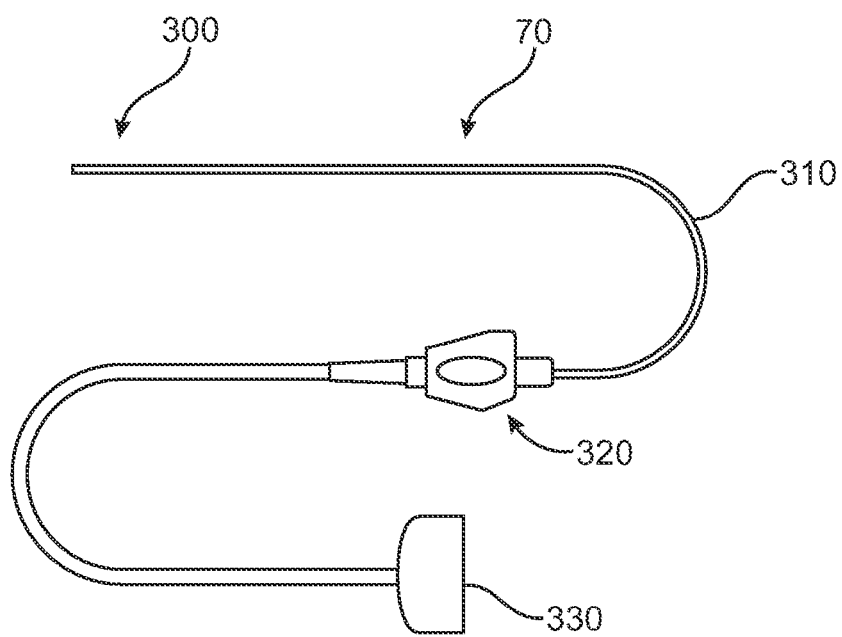
FIG. 3B illustrates features of an exemplary ultrasound probe of the visualization and ablation system of FIG. 3A.

The ultrasound probe 300 embodying features of the present invention, as shown in FIG. 3B, generally includes the imaging insert 70 as generally described above, and is connectable to an imaging insert probe port 212 at the delivery system proximal end 22. The ultrasound probe 300 includes an alignment element 320 for removably engaging with the system probe port 212 of the delivery system 210 through a probe cable 310. Alignment element 320 is connectable to the ultrasound system 500 by way of an ultrasound probe attachment element 330.

Figure 3C:
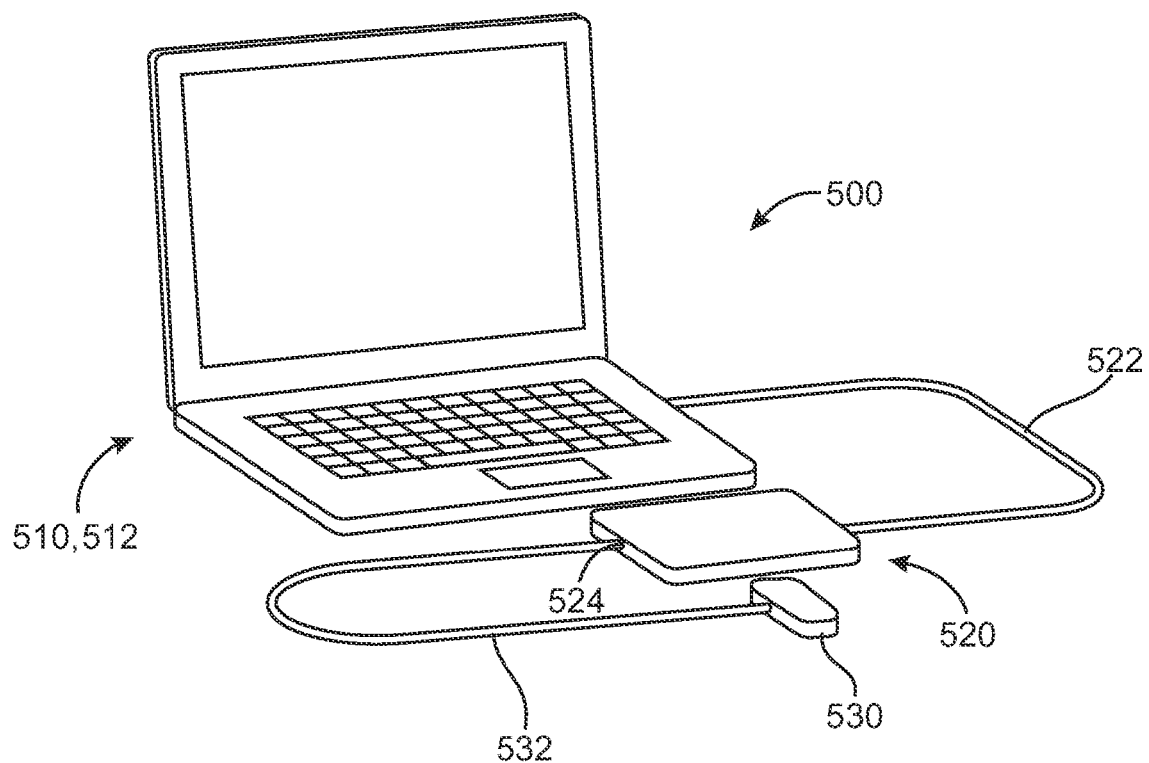
FIG. 3C illustrates features of an exemplary ultrasound system of the visualization and ablation system of FIG. 3A.

The ultrasound system 500, embodying features of the present invention, as shown in FIG. 3C, generally includes a CPU 510 such as one shown operatable by a laptop computer 512. The CPU 510 is connectable to a beam former 520 by way of a communications cable (such as a firewire cable) such as an ultrasound cable 522. The beam former 520 at a beam former distal end 524 is connectable to a probe attachment element 530 by a probe extension cable 532.

Figure 3D:
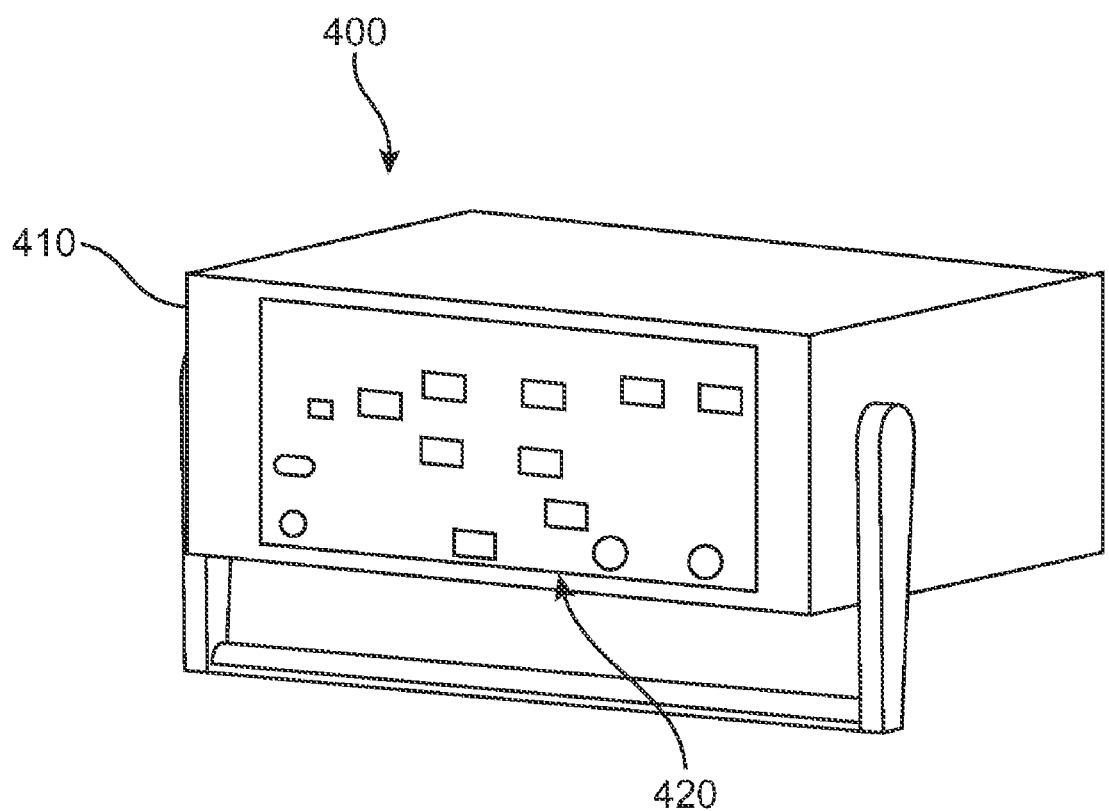
FIG. 3D illustrates features of an exemplary radio frequency energy generator of the visualization and ablation system of FIG. 3A.
Figure 3E:
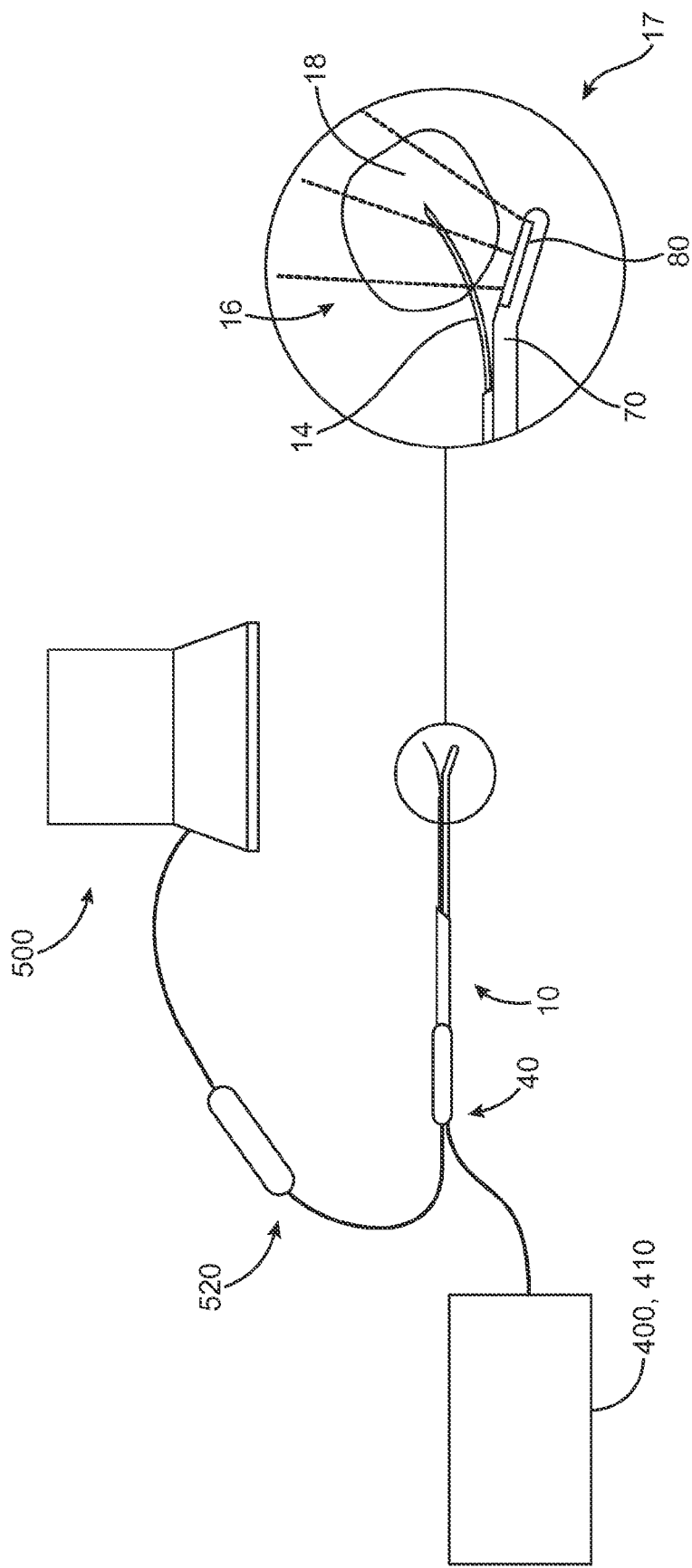
FIG. 3E illustrates the visualization and ablation system of FIG. 3A as disposed during operation within a uterus for the treatment of fibroids in accordance with the features of the present invention.

The radio frequency energy 410, embodying features of the present invention, and as shown in FIGS. 3D and 3E, is generally connectable to the delivery system 210 including needle 14, through energy outlet port 420. A suitable cable (not shown) removably connects energy outlet port 420 a needle port 413 at the proximal end 22 of the handle 40. Radiofrequency energy is delivered from the radio frequency generator 410 to fibroid 18 at the target site 16 through needle 14 which is disposed within the needle guide 58.

Figure 4A:
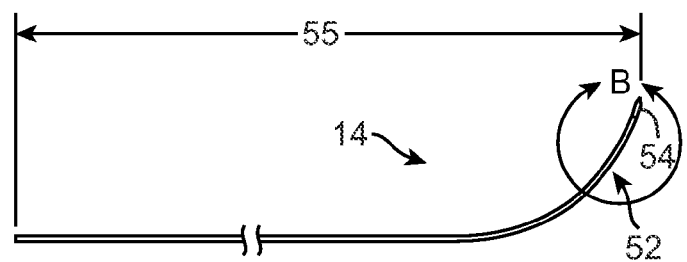
FIGS. 4A through 4C illustrate the exemplary features of an ablation needle for use with the visualization and ablation system of FIG. 3A.
Figure 4B:
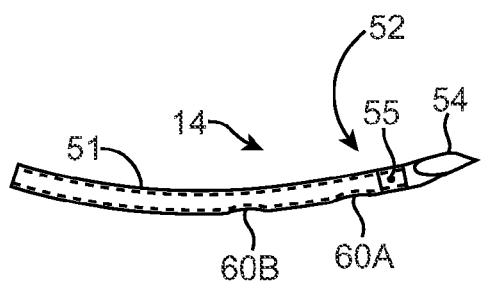
Figure 4C:

Now referring to FIGS. 4A-4C, needle 14 embodying features of the present invention, is shown disposed within the needle guide 58 which extends along the exterior of shaft 24. As further shown in cross-sectional FIGS. 5A-5C, the curved needle 14 generally comprises a two-piece construction including the elongate needle hollow body 50 with the shaped needle distal end 52 and the solid needle distal tip 54. The needle distal tip 54 may be laser welded 55 to the needle hollow body 50 as shown in FIG. 4B. The needle distal tip 54 may also be attached via alternative means, for example adhesives or mechanical features or fits. Generally the needle hollow body 50 will have a length 55 in a range from about 20 cm to about 45 cm, an oval cross section having a thickness 57 in a range from about 0.5 mm to about 2 mm, and a wideness 59 in a range from about 1 mm to about 3 mm. In an embodiment, as shown in FIG. 5A, the oval cross section is flattened minimizing lateral deflection during deployment or penetration of the needle 14. In an embodiment, as shown in FIGS. 4B and 5C, there are two laser cut infusion apertures 60 within the tubular body 50 for the infusion of agents (e.g., electrolytes, drugs, etc., dyes/contrasts) so as to enhance either or both the visualization and therapeutic effect of the needle 14 prior to, during, or after the ablation treatment. The infusion apertures 60 may be aligned on one side of the tubular body 50. Generally, the infusion apertures have a length 63 in a range from about 0.5 mm to about 2 mm and a width 65 in a range from about 0.5 mm to about 2 mm.

The needle body 50 is formed from an RF energy conductive material such as stainless steel. As will be appreciated, the solid tip 54 may comprise a variety of dimensions and shapes and is not limited to FIGS. 4A-4C and 5A-5C. It will be further appreciated that the tip 54 need not be a separate component but may alternatively be integrally formed with the needle body 50. The needle 14, including the tip 54 and tubular body 50 may be formed from a variety of materials including stainless steel, nitinol, and like for transmitting ablation energy. As best seen in FIG. 1A, the handle 40 may have a needle advancement portion to reciprocatably advance or retract the needle 14 from within the needle guide 58. The needle advancement portion, as shown, is in partially advanced position for complete deployment of the needle 14. The needle guide 58 will further have an oval cross section similar to that of the needle 14, with a thickness in a range from about 0.5 mm to about 2 mm and a wideness in a range from about 1 mm to about 3 mm. The flattened guide 58 and flattened needle 14 as shown in FIG. 4C are intended to minimize lateral deflection during deployment or penetration of the needle 14 into the tissue.

Figure 6A:
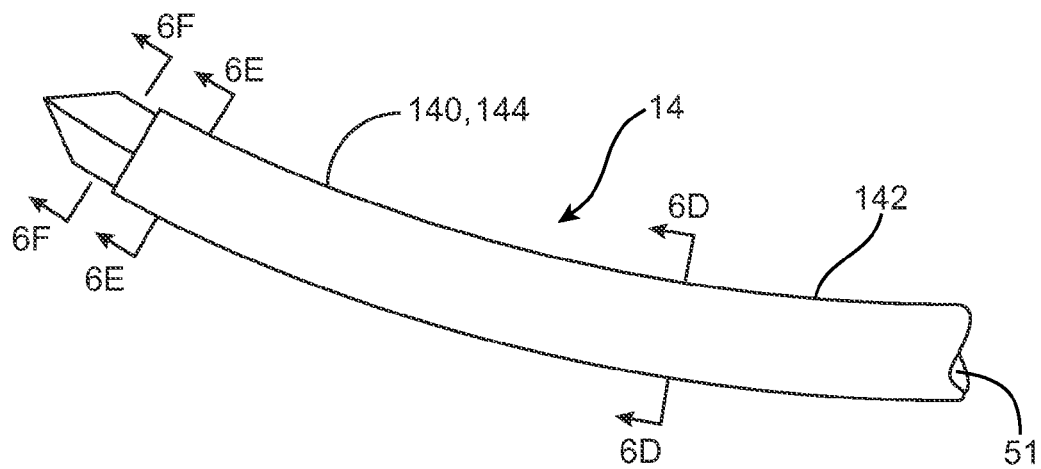
FIG. 6A illustrates an exemplary ablation needle for use with the visualization and ablation system of FIGS. 3A and including an insulating material such as a retractable sheath.
Figure 6B:
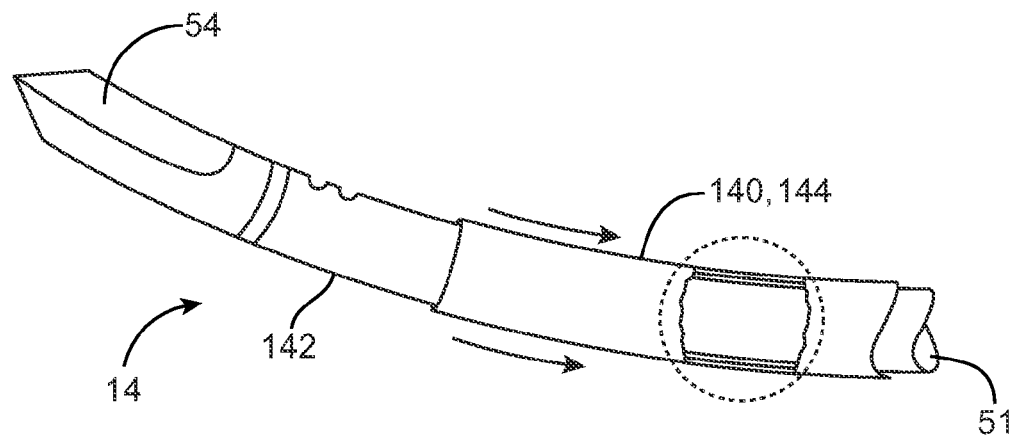
FIGS. 6B through 6C illustrate the needle of FIGS. 6A with the retractable sheath in a retracted position.
Figure 6C:
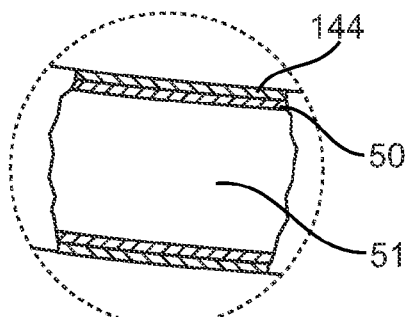
Figure 6D:
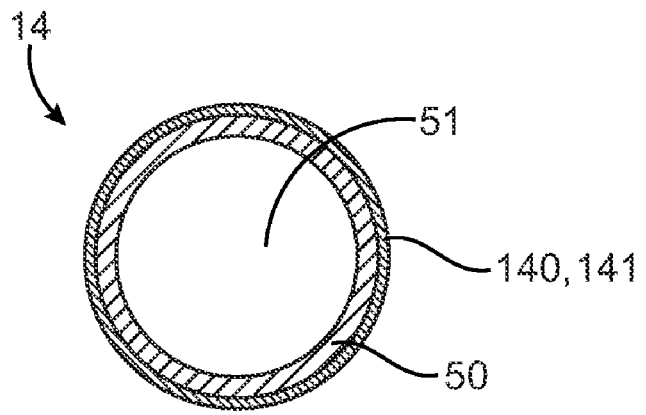
FIGS. 6D through 6F are cross-sectional views of the needle of FIG. 6A taken along lines 6D-6D, 6E-6E, and 6F-6F.
Figure 6E:
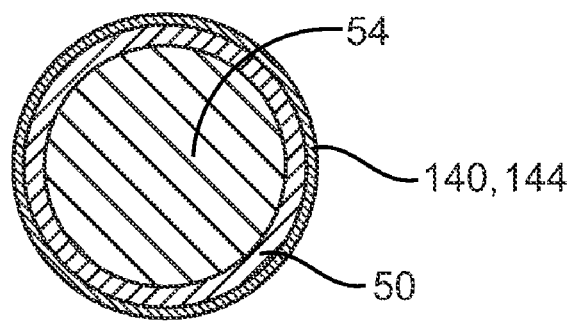
Figure 6F:
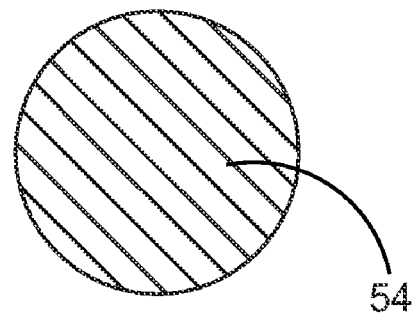

In an embodiment, as shown in FIGS. 6A-6C, an insulating material 140 extends longitudinally along at least an exterior portion 142 of the needle 14 terminating proximal to the conductive needle distal tip 54. In an embodiment, features of which are shown in FIGS. 6D-6E, the insulating material 140 forms a retractable sheath 144. The needle conductive needle distal tip 54 is extendable from a distal end 146 of the retractable sheath 144. The proximal retraction of the sheath 144 may be used to selectively control the length of the needle distal tip 54. As shown, the needle distal tip 54 is in a configuration distally extended from the distal end 146 of the retracted sheath 144.

The insulating sheath 140 may be formed from one or more suitable insulating material such as polyester shrink tubing, and Parylene ®(vapor deposited poly(p-xylene) polymer) coating such as Parylene ®C. Generally, the length of the conductive distal tip 54 ranges from about 1 to about 4 cm, usually from about 2 to about 3 cm, normally about 2 cm. In an embodiment, the conductive distal end is a T-type active electrode.

Now referring back to FIGS. 3D-E, the radio frequency energy generator 410 is configured to deliver power to the fibroid 18 at the target site 16, in a an amount ranging from about 1 to about 50 W, generally from about 10 to about 40 W, usually from about 20 to about 40 W, normally about 30 W. In an embodiment, the radio frequency energy generator 410 is configured to deliver and/or maintain a target temperature to the target site 16 ranging from about 50 to about 110° C., usually from about 60 to about 100° C., normally about 90° C.

The target site 16, such as fibroid 18, generally has an initial untreated diameter greater than about 2 cm, usually from about 1 to about 6 cm, normally about 2 cm. During the treatment of the fibroid 18, the needle 14 may be inserted one or more times into the tissue as may be necessary. In an embodiment, the needle distal tip 54, may be deployed into the tissue, up to 3 cm as measured from the distal end of the of the delivery device 10. During the treatment, the deployed length of the needle penetrating the tissue is visualized through the ultrasound imaging system 500.

By way of operation, in an embodiment, the deflectable distal tip 26 of the rigid shaft 24 may be deflected by the use of pull or tensioning wire(s) housed within the shaft 24. In another embodiment, the distal tip may have pre-determined deflection as compared to a longitudinal axis at a proximal portion of the device. Deflection may occur at a true mechanical pivot or at a flexible zone at the shaft distal end. When the delivery shaft 24 is deflectable by a user, various needles 14 may be used to match the amount of deflection provided by the distal tip 26 as well as the amount of tilt provided by the ultrasound array 80. Hence, the needle guide 58 may be empty until the distal end 26 of the shaft 24 is deflected. For example, the shaft 24 may be inserted in a straight configuration. The distal tip 26 may then be deflected until a target anatomy is identified. A needle 14 is then back loaded within the guide passage 70 that corresponds to the amount of the deflection. Alternatively, the needle may be pre-loaded in the shaft to provide a sterile and convenient delivery device to the user.

In exemplary embodiments, the therapeutic needle 14 advancement from the guide 58 via needle advancement portion on the shaft handle 40 can be viewed in the ultrasound system 500 in real time as it is penetrated into the uterine fibroid 18 inside the uterus 17. The therapeutic needle 14 may be penetrated in several configurations (e.g., lateral, side, axially extending) depending on the ultrasound viewing angle. Advantageously, tilting of the ultrasound array 80 and angling of the distal tip 26 allows a treating physician to image most or all of the cornua and fundus of the uterus 17 with a single device 10.

Although certain exemplary embodiments and methods have been described in some detail, for clarity of understanding and by way of example, it will be apparent from the foregoing disclosure to those skilled in the art that variations, modifications, changes, and adaptations of such embodiments and methods may be made without departing from the true spirit and scope of the invention. Therefore, the above description should not be taken as limiting the scope of the invention which is defined by the appended claims.

What is claimed is:

1. A system for visualization and ablation of fibroid tissues within a patient's body, comprising:
    an ultrasound imaging insert having a distal end with a flat surface;
    a rigid shaft having a proximal end, a distal end, a longitudinal axis, an axial passage extending through the rigid shaft and configured for removably receiving the ultrasound imaging insert therein, said passage having a flat inner surface at its distal end, said flat inner surface being asymmetrically inclined relative to the longitudinal axis for engaging the flat surface on the insert and axially and/or rotationally orienting the ultrasound insert when said insert is received within said axial passage, wherein the flat surface of the insert contacts the flat inner surface of the shaft after the insert is fully received in said axial passage; and
    a needle extending adjacent to an exterior surface of the rigid shaft and having a body and a distal tip and configured to deliver radiofrequency energy to a target site within the patient's body.

2. The system of claim 1, wherein at least a portion of the needle distal tip is an exposed conductive distal tip.

3. The system of claim 2, wherein the needle exposed conductive distal tip is distally extendable from a distal end of a retractable sheath extending on at least a portion of the exterior surface of the needle.

4. The system of claim 2, wherein at least a portion of the needle extending proximally from the exposed conductive distal end has a non-conductive coating thereon.

5. The system to claim 2, wherein the needle exposed conductive distal tip has an axial dimension ranging from 5 mm to about 3 cm.

6. The system of claim 1, wherein a retractable sheath extends on at least a portion of an exterior surface of the needle.

7. The system of claim 1, further comprising a radio frequency energy generator configured to deliver energy at a power ranging from about 1 to about 50 Watts.

8. The system of claim 7, wherein the radio frequency energy generator is configured to deliver energy at a power ranging from about 10 to about 40 Watts.

9. The system of claim 7, wherein the radio frequency energy generator is configured to deliver energy at a power ranging from about 20 to about 40 Watts.

10. The system of claim 7, wherein the radio frequency energy generator is configured to deliver energy at a power of about 30 Watts.

11. The system of claim 7, wherein the radio frequency energy generator is configured to provide a target temperature ranging from about 50 to about 110 degrees Celsius (° C.) at the target site.

12. The system of claim 7, wherein the radio frequency energy generator is configured to provide a target temperature ranging from about 60 to about 100 ° C. at the target site.

13. The system of claim 7, wherein the radio frequency energy generator is configured to provide a target temperature of about 90° C. at the target site.

14. The system of claim 7, wherein the radiofrequency energy generator is configured to deliver sufficient energy to ablate target tissue having an initial approximate diameter greater than about 2 centimeters (cm).

15. The system of claim 14, wherein the energy delivered to the target site is sufficient to ablate target tissue having an initial approximate diameter ranging in size from about 1 to about 6 cm.

16. The system of claim 14, wherein the energy delivered to the target site is sufficient to ablate target tissue having an initial approximate diameter of about 2 cm.

17. The system of claim 14, wherein the energy is delivered for a period of time so as to maintain a target temperature in the target site for a duration of time of about 6 minutes.

18. The system of claim 17, wherein the radiofrequency energy generator is configured to maintain a target temperature in the target site for a period of time ranging from about 1 to about 10 minutes.

19. The system of claim 18, wherein the energy is delivered for a period of time so as to maintain a target temperature in the target site for a period of time ranging from about 1 to about 8 minutes.

20. The system of claim 18, wherein the energy is delivered for a period of time so as to maintain a target temperature in the target site for a period of time ranging from about 5 to about 8 minutes.

21. The system of claim 18, wherein the energy is delivered for a period of time so as to maintain a target temperature in the target site for a period of about 6 minutes.

22. The system of claim 1, wherein the needle is disposed within a needle guide extending along an exterior of the rigid shaft.

23. The system of claim 1, wherein at least one external fluid lumen configured to deliver fluids for enhancing acoustic coupling between the ultrasound imaging insert and the target site, extends along at least a portion of the rigid shaft and terminates at an external port in fluid communication with an exterior of the system.

24. The system of claim 1, wherein at least one internal fluid lumen configured to deliver fluids for enhancing acoustic coupling between the ultrasound imaging insert and the target site, extends along at least a portion of the rigid shaft and terminates at an internal port within the axial passage.

25. The system of claim 1, wherein at least one fluid lumen extends along at least a portion of the rigid shaft and terminates at an external port at a distal portion of the needle at a shaft distal portion, the at least one lumen for delivery of contrasting dyes to target site.

26. A system for visualization and ablation of fibroid tissues within a patient's body, comprising:
    an ultrasound imaging insert having an ultrasound array with a flat surface at its distal end;
    a delivery system comprising a rigid shaft having a proximal end, a distal end, a longitudinal axis, an axial passage extending through the rigid shaft and configured for removably receiving the ultrasound imaging insert, said passage having a flat surface at its distal end, said flat inner surface being asymmetrically inclined relative to the longitudinal axis for engaging the flat surface on the insert and axially and/or rotationally orienting the ultrasound insert when said insert is received within said axial passage, wherein the flat surface of the insert contacts the flat inner surface of the shaft after the insert is fully received in said axial passage; and a needle extending adjacent an exterior surface of the rigid shaft and having a body and a distal tip;

a radio frequency energy generator attachable to the needle and configured to deliver to a target site within the patient's body radio frequency energy;

an ultrasound system including a central processing unit connectable to the ultrasound insert.

* * * * *